(12) United States Patent
Ullrich et al.

(10) Patent No.: US 6,837,900 B2
(45) Date of Patent: Jan. 4, 2005

(54) TANNING MODULE WITH HOUSING

(75) Inventors: Bernd Ullrich, Erlensee (DE); Ulrich Berger, Biebergemünd (DE)

(73) Assignee: Heraeus Noblelight GmbH, Hanau (DE)

( * ) Notice: Subject to any disclaimer, the term of this patent is extended or adjusted under 35 U.S.C. 154(b) by 134 days.

(21) Appl. No.: 10/256,404

(22) Filed: Sep. 27, 2002

(65) Prior Publication Data

US 2003/0078635 A1 Apr. 24, 2003

(30) Foreign Application Priority Data

Oct. 24, 2001 (DE) ........................................ 101 51 850

(51) Int. Cl.[7] .............................................. A61N 5/06
(52) U.S. Cl. ........................... 607/91; 607/88; 607/90; 606/9; 606/10; 362/362; 362/365; 362/373; 362/374; 362/377
(58) Field of Search ............................. 607/88–91, 93, 607/94; 606/9, 10, 13, 2, 22; 362/26, 31, 362–367, 370–375

(56) References Cited

U.S. PATENT DOCUMENTS

| | | | | |
|---|---|---|---|---|
| 4,298,005 A | * | 11/1981 | Mutzhas | 607/94 |
| 5,425,754 A | * | 6/1995 | Braun et al. | 607/88 |
| 5,632,768 A | * | 5/1997 | Shimada | 607/96 |
| 5,720,772 A | * | 2/1998 | Eckhouse | 607/88 |
| 5,743,632 A | * | 4/1998 | Carl | 362/294 |
| 5,961,543 A | * | 10/1999 | Waldmann | 607/88 |
| 6,228,074 B1 | * | 5/2001 | Almeida | 606/9 |
| 6,649,921 B1 | * | 11/2003 | Cekic et al. | 250/504 R |
| 6,717,164 B2 | * | 4/2004 | Ullrich et al. | 607/88 |

FOREIGN PATENT DOCUMENTS

| | | |
|---|---|---|
| DE | 29 41 467 A1 | 4/1981 |
| DE | 36 31 427 C2 | 4/1987 |
| DE | 39 27 695 C2 | 2/1991 |
| DE | 40 37 483 C2 | 5/1992 |
| DE | 92 10 776 U | 12/1992 |
| DE | 43 23 936 A1 | 1/1995 |
| DE | 195 16 603 A1 | 11/1996 |
| FR | 711 054 A | 9/1931 |

* cited by examiner

*Primary Examiner*—A. Farah
(74) *Attorney, Agent, or Firm*—Fulbright & Jaworski L.L.P.

(57) ABSTRACT

The invention relates to a tanning module with optimized guidance of the cooling air, having a housing, a three-dimensional reflector, and at least one windowpane-shaped radiation filter. The housing has on the side of the housing opposite the radiation filter the shape of a gable roof, a hip roof, or a false hip roof, the roof ridge being flattened and facing away from the radiation filter.

44 Claims, 6 Drawing Sheets

TANNING MODULE WITH HOUSING

BACKGROUND AND SUMMARY OF THE INVENTION

The invention relates to a tanning module having a housing, a three-dimensional reflector disposed in the housing, and at least one discoid radiation filter, wherein the at least one radiation filter covers the radiation issuance surface of the reflector and is disposed on a first side of the housing, at least one opening being provided in the reflector for the installation and electrical connection of a tanning radiator, and the reflector having its maximum cross section in the area of the radiation issuance surface.

Such tanning modules are disclosed, for example, in DE 29 41 487 A1, wherein a rectangular housing including blower and power conducting plates are inserted in the housing. The rectangular housing is divided into an air intake side and an exhaust side, the tanning radiator being arranged on the exhaust side and indirectly cooled. The intake of cooling air which flows along the filter plate and cools it takes place on the air intake side of the housing. The cooling air leaves from the exhaust side of the housing through the same side wall as it previously entered the housing on the intake side.

DE 195 16 603 A1 discloses a low-pressure face area for tanning apparatus, wherein a rectangular housing including reflector and filter plate is used. The housing is suitable for the installation of several UVC tubes. The entry of cooling air into the housing takes place through an opening between housing and filter plate, the cooling air flowing along the tubes and leaving the housing at the back of the housing.

DE 36 31 427 C2 describes a radiating apparatus with a rectangular housing and reflector as well as filter plate. This is a low-power apparatus, so that cooling of the tanning radiator or reflector is not provided for. To secure the filter against breakage a push switch is provided which is held by the filter plate in its depressed position, but in the event of breakage departs from this position and shuts off the power source.

DE 39 27 695 C2 discloses a tanning apparatus with a pivotally arranged interference filter. In the direction of the exit of the radiation an infrared filter follows the interference filter. Depending on the tilt of the interference filter in the radiation exit the limit of the transmission spectrum toward the short-wavelength UV-B content or to the longer wavelength content. Thus the radiation spectrum is adjustable to the skin type of the person being irradiated is adjustable by tilting the filter.

DE 40 37 483 C2 describes an ultraviolet radiation apparatus with protection against breakage for a glass filter plate, a current-carrying electrical conductor pathway being disposed on its circumference. If the filter glass breaks the conductor pathway is broken and shuts off the tanning radiator.

The problem is to offer a tanning module which has a housing with optimized conduct of the cooling air.

The problem is solved in that the housing is equipped on a second side in the form of a gable roof, a hip roof, or a false hip roof, the roof ridge being flattened and facing away from the radiation filter.

Such a housing form has the advantage that the free cross section between the outside of the reflector and the inside of the housing can be kept small, so that when air is drawn from the area behind the reflector a relatively uniform distribution of the flow develops. The temperature of the reflector is thus made uniform. In the tanning module of the invention additional flow baffles can be dispensed with, since the roof forms can permit the elimination of "dead corners" in the air flow. In the area of the opening of the reflector, which serves for the insertion and connection of a tanning radiator, air can also be drawn out of the reflector chamber and thus the tanning radiator can be directly cooled.

The tanning module according to the invention is suitable for use as a tanning radiator with an electrical power ranging from 250 W to 1000 W. It is outstandingly suitable for use in a great variety of tanning apparatus or medical apparatus for irradiating the face, the throat area, the body area, the leg or foot area. Also possible is its installation in ceilings, for example for the irradiation of reclining areas from great distances. The tanning module of the invention can basically be mounted in any kind of holder, so that it can radiate in all directions in a virtual sphere. Several tanning modules can be mounted side by side or in series in order to produce a larger irradiation field. It is possible to operate with a separate fan for each tanning module, or else to operate several tanning modules with a central fan.

The radiation filter is preferably aligned parallel to the radiation issuance surface of the reflector.

The flattened roof ridge can be formed by a planar part of the housing wall, and the latter can be aligned parallel to the radiation filter. The flattened roof ridge, however, can also be formed by a vaulted part of the housing wall, and the latter can be curved concavely or convexly. It has been found especially useful if a rectangular area of the housing wall adjoins the gable roof, hip roof or false hip roof. The radiation filter can be accommodated in the latter, for example.

Especially preferred is a reflector of cupped or tub shape, the cup or tub bottom of the reflector being either curved or plane-parallel to the at least one radiation filter. A circumference of the reflector parallel to the radiation issuance surface describes preferably a circle, an ellipse, a rectangle or a polygon. In that case it is preferred if the reflector is formed of facets and the circumference of the reflector parallel to the radiation issuance surface describes a polygon with twelve sides.

Especially suited in that case is a reflector which has a height ranging from 90 mm to 95 mm, and is especially 93.6 mm high. The dodecahedron in the plane of the radiation issuance surface has preferably a maximum diameter (corner to corner) ranging from 210 mm to 230 mm and amounts especially to 210 mm.

Another suitable reflector has a height ranging from 110 mm to 125 mm and is especially 118.7 mm high. The dodecahedron in the plane of the radiation issuance surface has preferably a maximum diameter (corner to corner) ranging from 170 mm to 200 mm and amounts especially to 184 mm.

Another suitable reflector has a height ranging from 75 mm to 90 mm and is especially 83.3 mm high. The dodecahedron in the plane of the radiation issuance surface has preferably a maximum diameter (corner to corner) ranging from 205 mm to 235 mm and amounts especially to 220 mm.

The conduction of the cooling air flow in the housing is especially optimized if at least one air exhaust opening is present in the area of the roof slopes. In that case a flange can be applied at the air exhaust opening. To draw cooling air out of the housing an air exhaust tube can be arranged on the flange. With an air exhaust tube of this kind a central or off-center air exhaust is possible.

To be able to adjust the exhaust for the tanning module, a reducing plate may be present to reduce the air exhaust opening. This is useful when several tanning modules are used and they are at various distances away from a central fan, i.e., one used by all tanning modules simultaneously, or the air is exhausted to the fan in a kind of series circuit from one tanning module through at least an additional one.

Preferably, at least one mounting for electrical connections or components is disposed on the housing, such components being here, for example, an igniter, a pushbutton switch or a grounding lug.

It is especially preferred to arrange an air intake plate between housing and reflector, the radiation issuance surface of the reflector being shifted up or down from the plane of the air intake plate, at least one intake opening being formed between the intake plate and the reflector and the exhaust plate having an opening for the reflector, which in vertical projection onto the at least one radiation filter has the size of the radiation issuance surface of the reflector. Through this arrangement of the reflector with reference to the intake plate, an annular intake opening is preferably formed between intake plate and reflector, through which cooling air can be drawn from the area between the radiation filter and the radiation issuance surface of the reflector toward the outer wall of the reflector, in which case a highly symmetrical alignment of the intake openings has a positive effect on the uniformity of the cooling of the reflector and radiation filter. The temperature distribution on the radiation filter has a decided influence on its transmission qualities.

It has also been found advantageous if an intake plate joins the housing and the reflector on all sides in the area of the radiation issuance surface, in which case the intake plate has at least one intake opening and also has an opening for the reflector, which in vertical projection onto the at least one radiation filter, has the size of the radiation issuance surface of the reflector.

In particular, the intake plate has a rectangular periphery, the periphery of the reflector describes a circle, an ellipse or a polygon parallel to the radiation issuance surface, and the at least one intake opening is disposed in the area of one corner of the intake plate.

It is preferred that four intake openings be formed in the intake plate and that one intake opening is arranged in each corner of the intake plate. It has proven to be aerodynamically advantageous if the at least one intake opening is enlarged along the sides of the intake plate. The intake opening can for that purpose be trapezoidal, for example, with the long side of the trapeze facing the reflector. The long side of the trapeze as well as its opposite side can be curved.

It has been found good to fasten the reflector to the housing only above the intake plate. Then different spacers can be provided between the intake plate and the reflector.

The at least one radiation filter is preferably removable from the housing by means of a swing mechanism. The swing mechanize is to permit the radiation filter to be tilted with respect to the housing, and it is to be possible to remove the radiation filter from the housing only after a displacement of the tilted radiation filter in the housing. Thus a user-friendly exchange of the radiation filter becomes possible, and also any abrupt falling out of the radiation filter is prevented, since with such a swing mechanism any dropping of the radiation filter and therefore its breakage is prevented.

The attachment of the radiation filter to the housing becomes especially simple if the at least one radiation filter is rectangular. Thus the at least one radiation filter is preferred with a length and a width in the range from 215 mm to 240 mm. Especially, the at least one radiation filter has a length of 230 mm and a width of 225 mm.

The at least one radiation filter is preferably an interference filter, since the UV content can be controlled and the visible part of the light can be suppressed.

It is optimal if at least one air intake opening is present between the at least one radiation filter and the housing an/or if at least one air intake opening is present in the housing between the at least one radiation and the reflector. Care must of course be taken that no unfiltered part of the radiation passes out of the housing through the air intake opening. Thus, cooling air can flow through the air intake opening in the area between the radiation filter and radiation issuance surface of the reflector and can be drawn from there through exhaust openings to the exterior of the reflector.

An embodiment of the tanning module is preferred in which a first radiation filter is present and a second radiation filter is plane-parallel thereto, the second radiation filter being disposed between the radiation issuance surface of the reflector and the first radiation filter, the first radiation filter being the interference filter. The second radiation filter is then preferably an ultraviolet filter or an infrared filter.

To prevent breakage of the at least one radiation filter, at least one pushbutton switch can be arranged on the housing to rest on the at least one radiation filter. The pushbutton switch can be guided through the reflector perpendicular to the radiation issuance surface thereof, or else through the intake plate perpendicular to the radiation issuance surface of the reflector. The pushbutton, however, can also be arranged on the intake plate and rest upon the at least one radiation filter. In the event of breakage of the monitored radiation filter, the change in the position of the pushbutton switch interrupts the power to the tanning radiator and the user is protected against an uncontrolled dose of radiation.

In the area of the opening in the reflector a socket is preferably provided for the mechanical and electrical connection of a tanning radiator.

Between the at least one radiation filter and the air intake plate a cover plate can be arranged which is spaced apart from the intake plate and which has an opening having, in its vertical projection onto the at least one radiation filter, the size of the radiation issuance surface of the reflector. This cover plate conceals from the user's eye any intake openings for cooling air that may be present in the intake plate.

It has been found especially desirable if the housing is rectangular in the area of the radiation filter and is closed off on all four sides with a lip, the four lips being aligned parallel to the radiation filter. Two oppositely lying lips of the four face the radiation filter and the other two oppositely lying lips face away from the radiation filter. Such a configuration is especially to be recommended when a plurality of tanning modules are used side by side in a tanning apparatus, so that especially the lips which face away from the radiation filter will block the view of the rear area of the tanning module from the transition between two tanning modules.

FIGS. 1 to 9 are intended to explain the tanning module of the invention by way of example.

DETAILED DESCRIPTION

Figure 1:
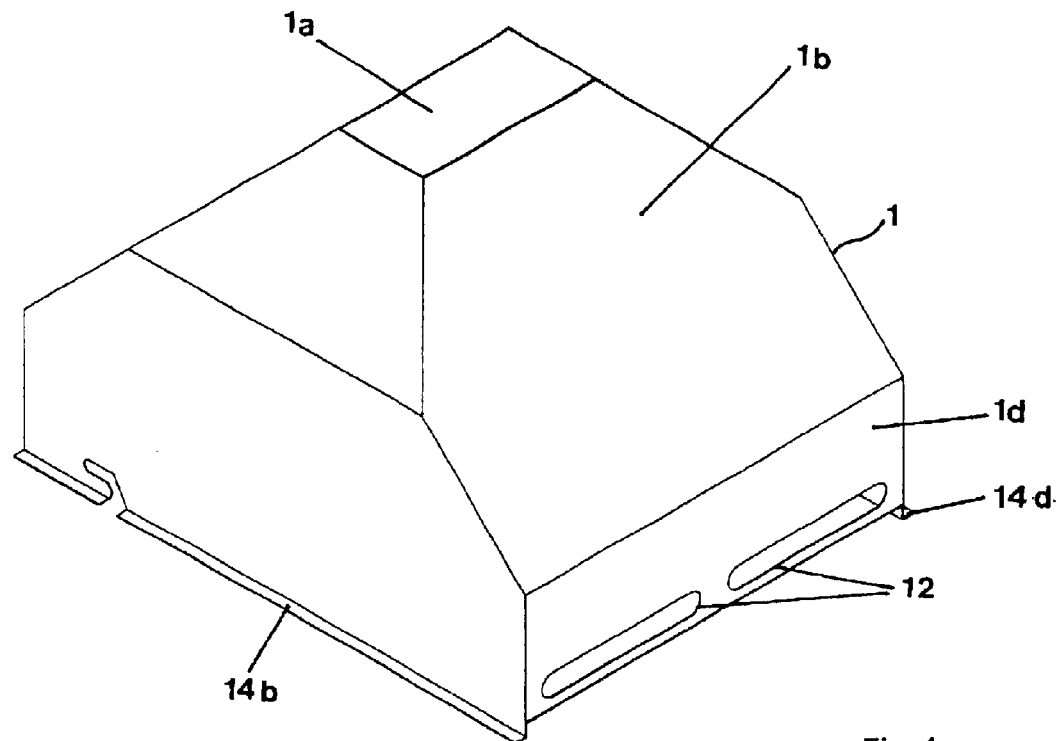
FIG. 1 shows the housing of a tanning module in a three-dimensional view.

Thus FIG. 1 of the housing 1 of a tanning module shows a three-dimensional view, wherein the shape of a false hip roof 1b with a flattened roof ridge 1a is seen. The roof structure is adjoined by a rectangular housing wall area 1d which ends in four lips, two lips 14b, 14d turned outward and the other two lips (not seen here) are turned inward. In the rectangular housing wall area 1d air intake openings 12 are present.

Figure 2:
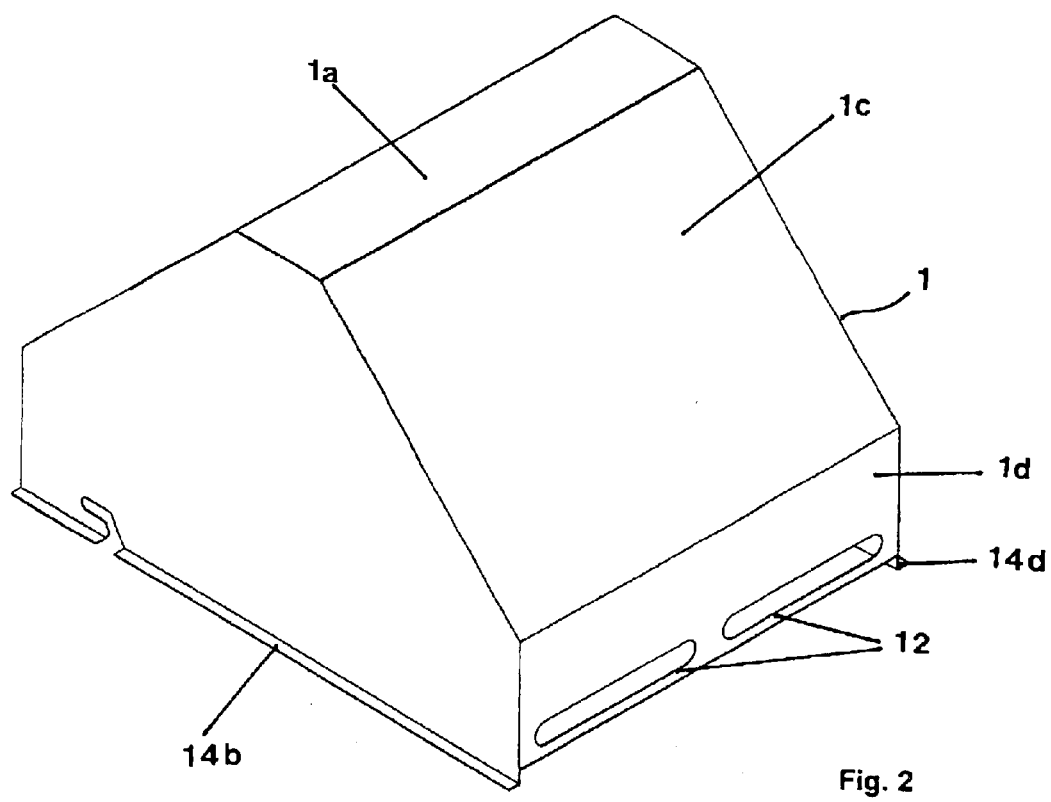
FIG. 2 another housing of a tanning module in a three-dimensional view.

FIG. 2 shows another housing 1 of a tanning module in a three-dimensional view wherein the shape of a gable roof 1c with a flattened roof ridge 1a.

Figure 3:
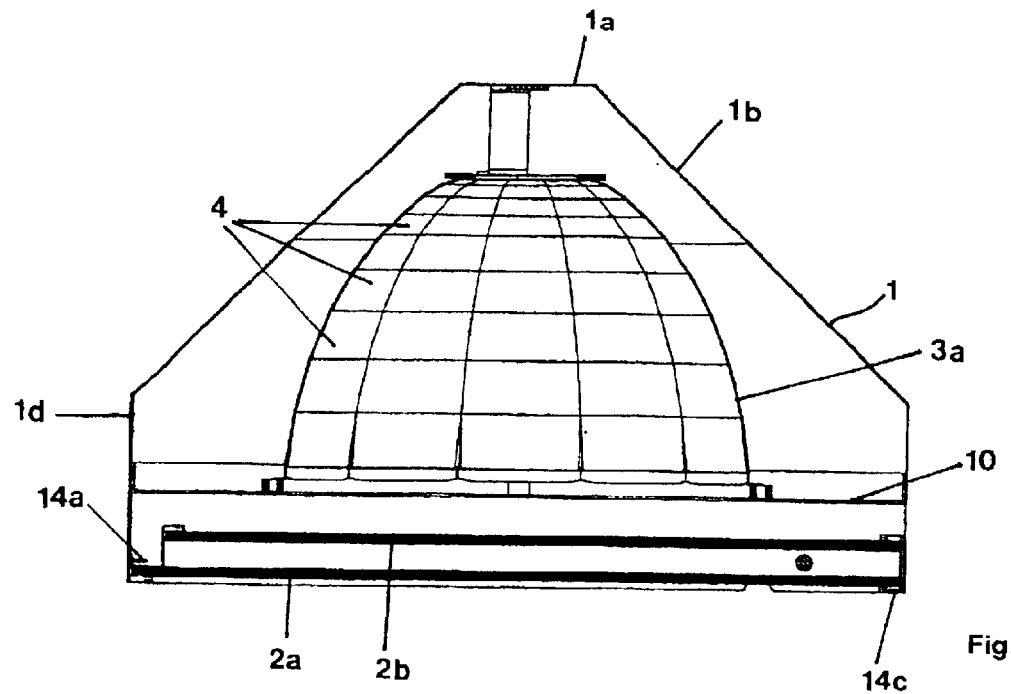
FIG. 3 a tanning module with a housing as in FIG. 1 in a section across the roof ridge.

FIG. 3 shows a tanning module with a housing 1 according to FIG. 1, in a section taken across the roof ridge, wherein a reflector 3a formed of facets 4 is present. The reflector 3a is connected by spacers to an air intake plate 10 whereby cooling air can be aspirated between the spacers into the space between reflector 3a and housing 1. In the rectangular housing wall area 1d there is a rectangular first radiation filter 2a and a rectangular second radiation filter 2b. Also, the lips 14a, 14c can be seen, which point toward the radiation filters.

Figure 4:
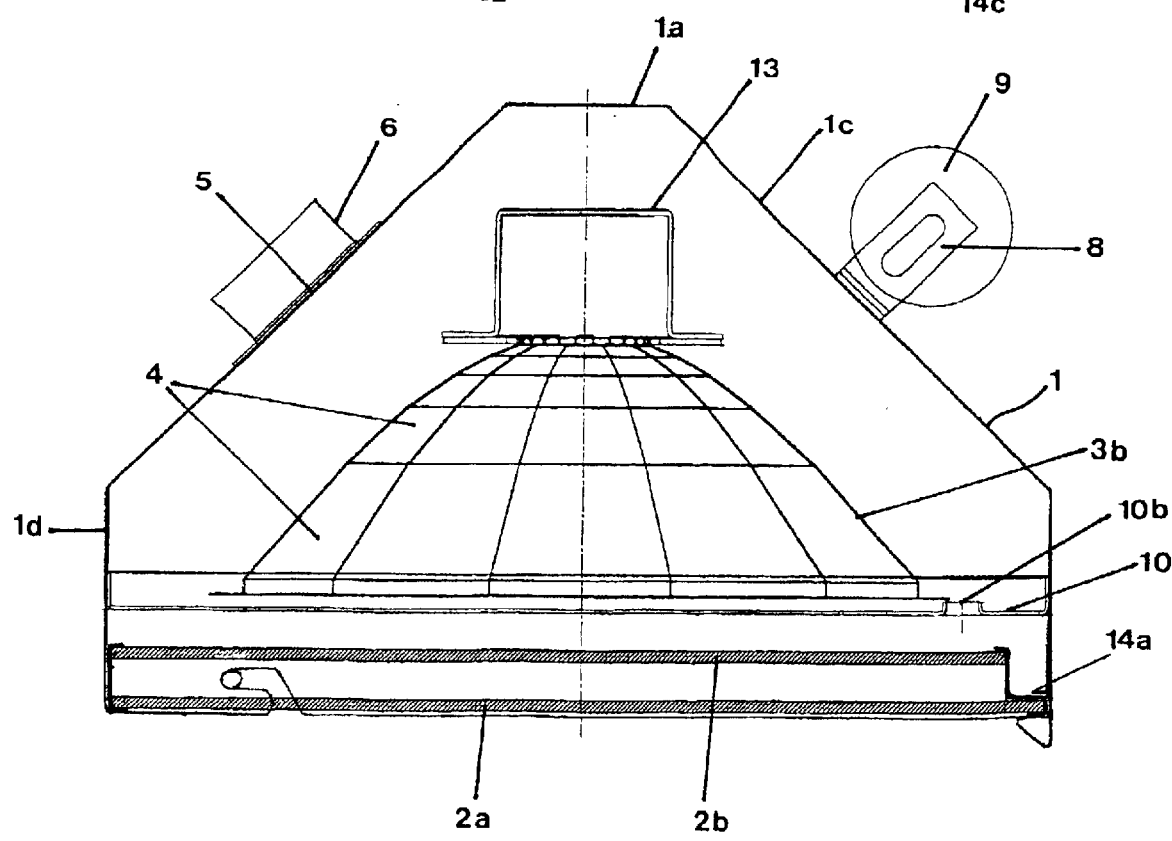
FIG. 4 a tanning module in section, with a housing according to FIG. 2.

FIG. 4 shows a tanning module with a housing according to FIG. 2 in a section taken across the roof ridge, a reflector 3b formed of facets 4 being present. The reflector 3b is connected to an air intake plate 10 through which cooling air can be drawn through intake openings into the space between the reflector 3b and housing 1. Furthermore, an opening 10b with a screw thread is present, through which a pushbutton switch can be placed on a radiation filter. In the rectangular housing area 1d a rectangular first radiation filter 2a and a rectangular second radiation filter 2b are present. Also, the socket 13 for receiving a tanning radiator in the opening of reflector 3b can be seen. In the slope of the roof there is an air intake opening 5 on which the flange 6 is attached. Moreover, a mount 8 is present for fastening an igniter 9.

Figure 5:
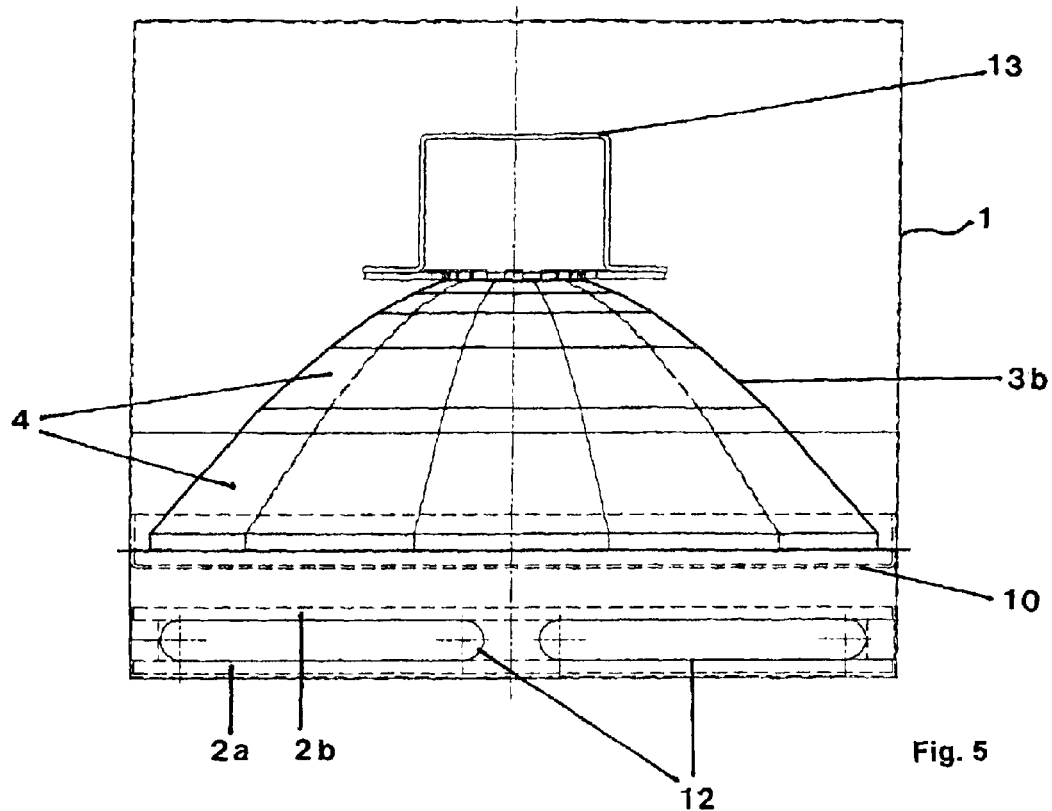
FIG. 5 a tanning module with a housing as in FIG. 1, in section along the roof ridge FIG. 6 another tanning module of FIG. 1 in a section along the roof ridge.

FIG. 5 shows another tanning module with a housing 1 according to FIG. 1 in a section taken along the roof ridge. The reflector 3b is connected to the housing 1 and spaced away from the air intake plate 10 and cooling air can be drawn in between the air intake plate 10 and the reflector 3b into the space between reflector 3b and housing 1.

Figure 6:
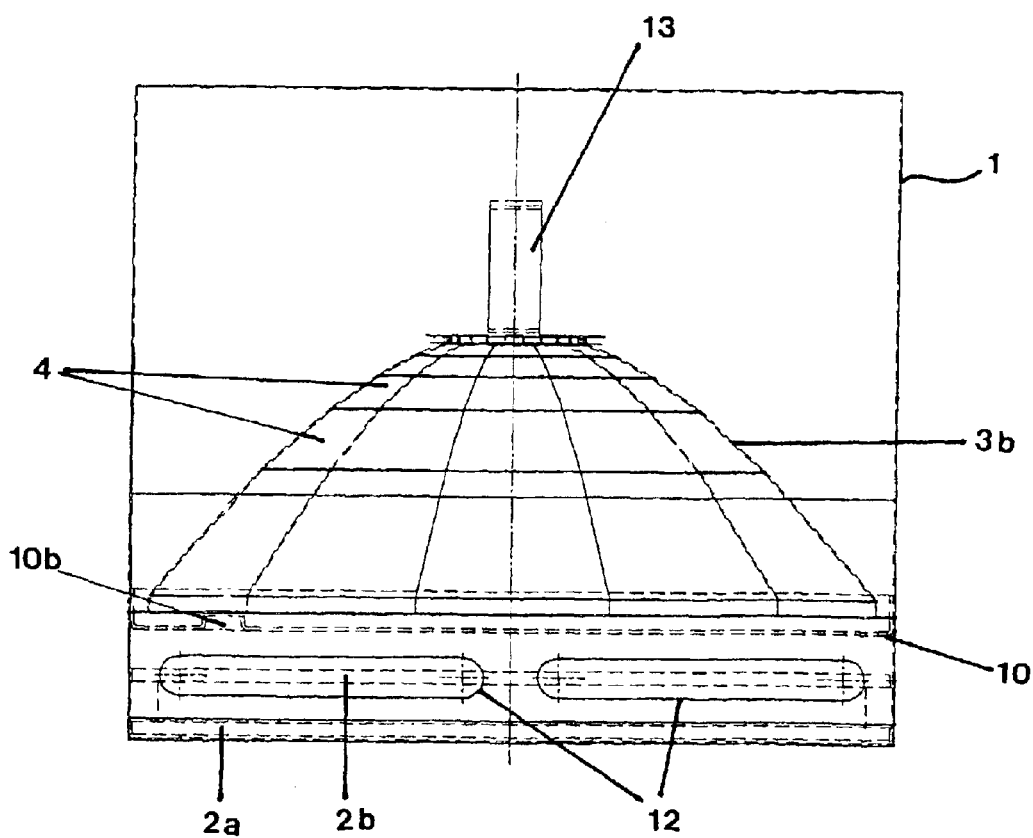

FIG. 6 shows another tanning module with a housing according to FIG. 2, in a section taken along the roof ridge. The reflector 3b is connected to the air intake plate 10 where cooling air can be drawn through air intake openings into the space between reflector 3b and housing 1.

Figure 7:
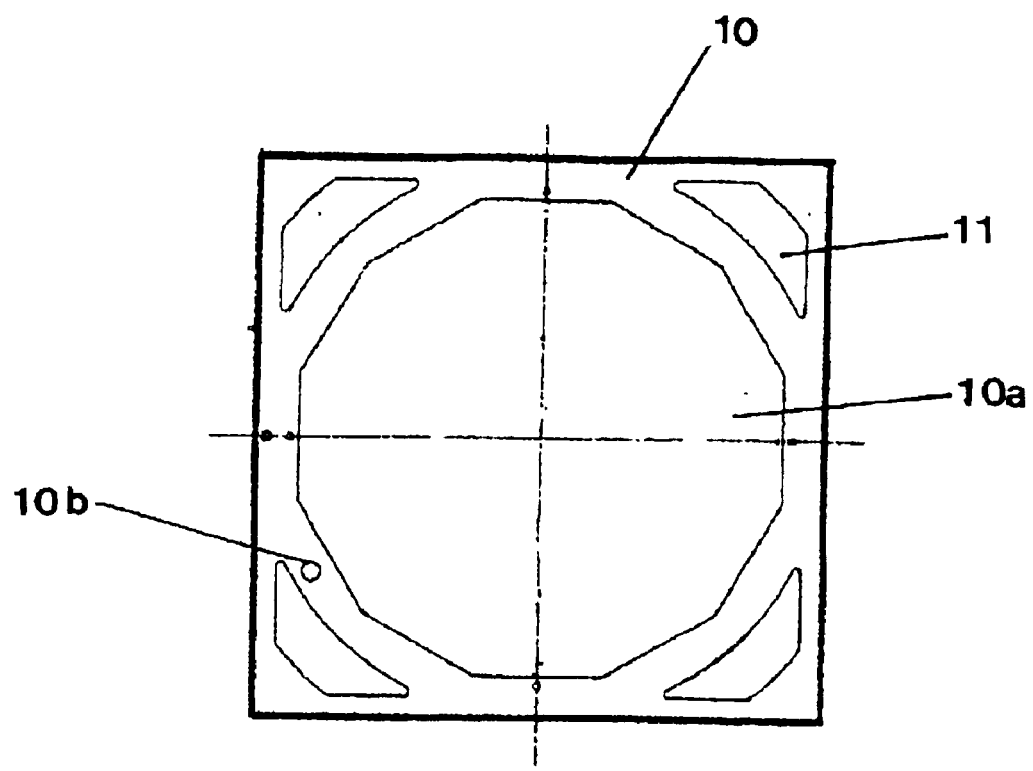
FIG. 7 an air intake plate including four intake openings.

FIG. 7 shows an air intake plate 10 including four intake openings 11, and an opening 10a is present for a twelve-sided reflector. Moreover, a threaded opening 10b is present, through which a pushbutton switch can be placed on a radiation filter.

Figure 8:
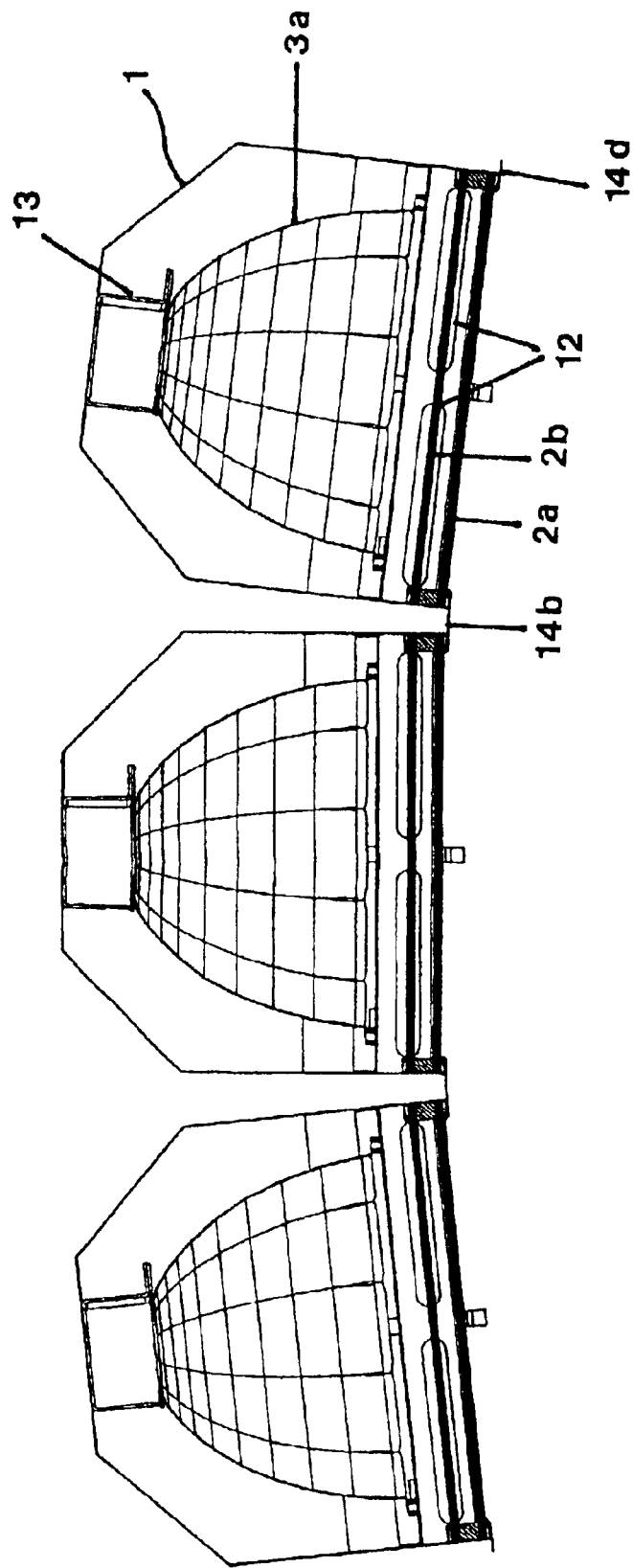
FIG. 8 three tanning modules in section.

FIG. 8 shows three tanning modules with housing as in FIG. 1, in a section through the roof ridge; the arrangement shows the joining of the lips 14b, 14d, from module to module.

Figure 9:
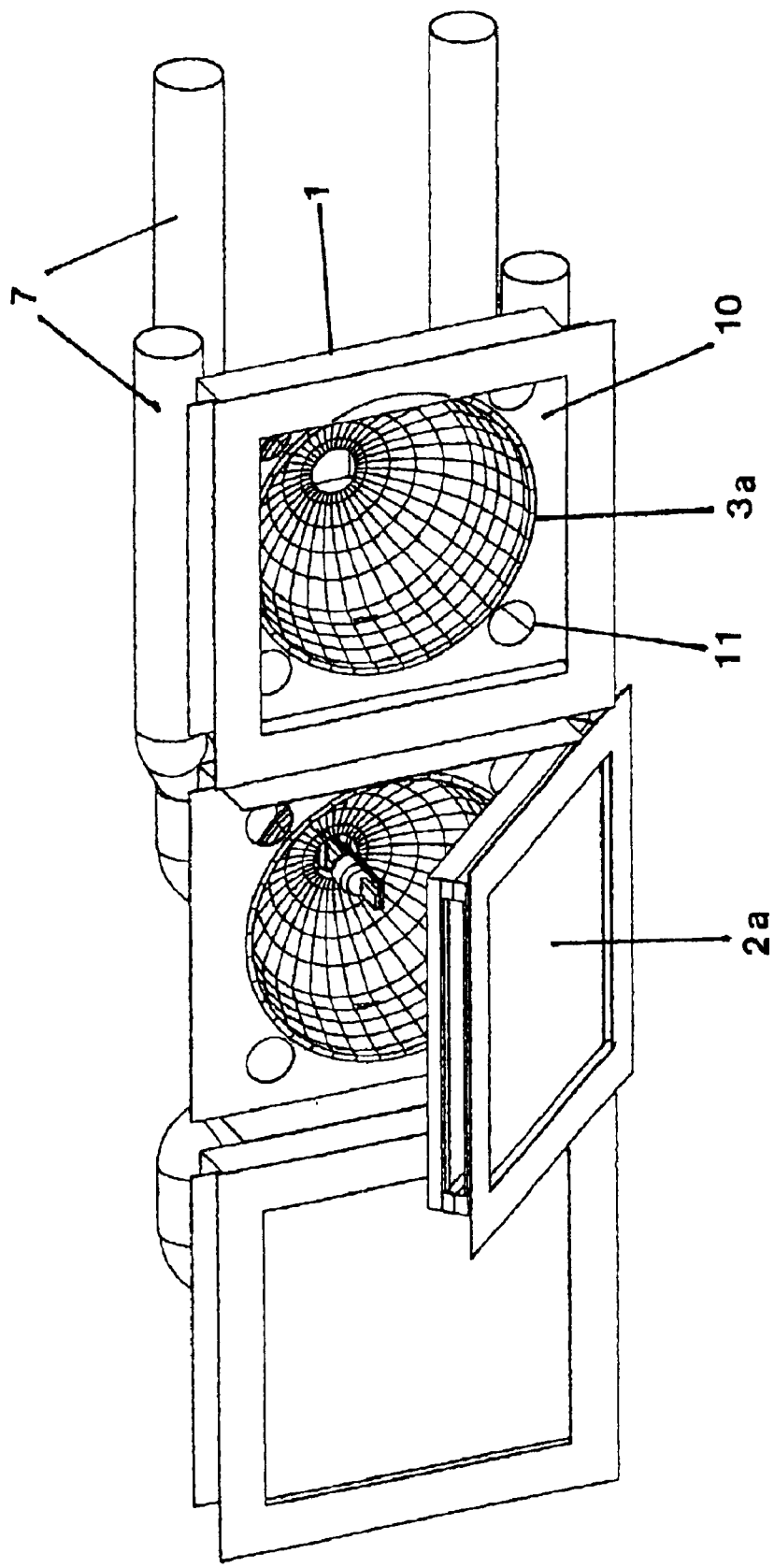
FIG. 9 a three-dimensional view of several tanning modules.

FIG. 9 shows a three-dimensional view of several tanning modules mounted side by side. On the far left is a tanning module with a closed radiation filter. In the middle there is shown a tanning module with an opened radiation filter 2a, including a tanning radiator, wherein the air intake plate 10 with circular intake openings 11 can be seen, as well as the reflector 3a. On the far right is shown a radiation filter without the tanning radiator. All three modules are provided with air exhaust tubes 7.

What is claim is:

1. A tanning module comprising a housing module with a housing, a three-dimensional reflector, and at least one discoid radiation filter, wherein the at least one radiation filter covers the radiation issuance surface of the reflector and is arranged on a first side of the housing, wherein at least one opening is provided in the reflector for the insertion and electrical connection of a tanning radiator, and wherein the reflector has its maximum cross section in the area of the radiation issuance surface, wherein the housing is configured on a second side opposite the radiation filter in the shape of a gable roof, a hip roof, a false hip roof, the roof ridge being flattened and disposed away from the radiation filter, wherein a space between the housing and reflector contains cooling air or fluid.

2. A tanning module according to claim 1, wherein the radiation filter is aligned parallel to the bottom of the radiation issuance surface of the reflector.

3. A tanning module according to claim 1, wherein that at least one mount for electrical connections or components is disposed on the housing.

4. A tanning module according to claim 1, wherein that the at least one radiation filter is releasable from the housing through a swing mechanism.

5. A tanning module according to claim 1, wherein that at least one air intake opening is present in the area of the circumference of the at least one radiation filter in the housing and/or between the housing and the radiation filter.

6. A tanning module according to claim 1, wherein that a socket is provided in the area of the opening of the reflector for the mechanical and electrical connection of a tanning radiator.

7. A tanning module according to claim 1, wherein the flattened roof ridge is formed by a planar housing wall part.

8. A tanning module according to claim 7, wherein the planar housing wall part is aligned parallel to the radiation filter.

9. A tanning module according to claim 1, wherein the flattened roof ridge is formed by an arched housing wall part.

10. A tanning module according to claim 9, wherein the arched housing wall part is configured concavely or convexly with respect to the radiation filter.

11. A tanning module according to claim 1, wherein a rectangular housing wall area adjoins the gable roof, hip roof or false hip roof in the direction of the radiation filter.

12. A tanning module according to claim 11, wherein the reflector is configured in a cup or tub-shape.

13. A tanning module according to claim 12, wherein the cup or tub bottom of the reflector is arched.

14. A tanning module according to claim 12, wherein that the cup or tub bottom of the reflector is made plane-parallel to the at least one radiation filter.

15. A tanning module according to claim 1, wherein that a periphery of the reflector parallel to the radiation issuance surface describes a circle, an ellipse, a rectangle or a polygon.

16. A tanning module according to claim 15, wherein that the reflector is formed of facets and the periphery of the reflector parallel to the radiation issuance surface, describes a polygon with twelve corners.

17. A tanning module according to claim 16, wherein that the reflector has a height of 90 mm to 95 mm, and the dodecahedron has a maximum diameter in the plane of the radiation issuance surface (corner to corner) ranging from 210 mm to 230 mm.

18. A tanning module according to claim 16, wherein that the reflector has a height ranging from 110 mm to 125 mm, and the dodecahedron has a maximum diameter in the plane of the radiation issuance surface (corner to corner) ranging from 170 mm to 200 mm.

19. A tanning module according to claim 16, wherein that the reflector has a height ranging from 75 mm to 90 mm, and the dodecahedron in the plane of the radiation issuance surface has a maximum diameter (corner to corner) ranging from 205 mm to 235 mm.

20. A tanning module according to claim 1, wherein that the housing has in the area of the roof slopes at least one air exhaust opening.

21. A tanning module according to claim 20, wherein that a reducing disk is present to reduce the size of the air exhaust opening.

22. A tanning module according to claim 20, wherein that a flange is applied to the at least one air exhaust opening.

23. A tanning module according to claim 22, wherein that an air exhaust tube is disposed on the flange.

24. A tanning module according to claim 1, wherein that an air intake plate is disposed between the housing and reflector, the radiation issuance surface of the reflector being shifted upward or downward to the plane of the air intake plate, at least one air intake opening being formed between air intake plate and reflector and the air intake plate having an opening for the reflector, which in its vertical projection onto the at least one radiation filter has the size of the radiation issuance surface of the reflector.

25. A tanning module according to claim 24, wherein that the reflector is fastened to the housing only through the air intake plate.

26. A tanning module according to claim 24, wherein that between the at least one radiation filter and the air intake plate a cover plate is disposed, which is spaced away from the air intake plate and which has an opening which, in its vertical projection onto the at least one radiation filter, has the size of the radiation issuance surface of the reflector.

27. A tanning module according to claim 1, wherein that an air intake plate connects the housing and the reflector on all sides in the area of the radiation issuance surface of the reflector, the air intake plate having at least one air intake opening and also en opening for the reflector, which in vertical projection onto the radiation reflector has the size of the radiation issuance surface of the reflector.

28. A tanning module according to claim 27, wherein that the air intake plate has a rectangular circumference, that the circumference of the reflector radiation issuance surface describes a circle, an ellipse or a polygon, and that the at least one air intake opening is disposed in the area of a corner of the air intake plate.

29. A tanning module according to claim 28, wherein that four air intake openings are formed in the air inntake plate and that an air intake opening is disposed in each corner of the air intake plate.

30. A tanning module according to claim 28, wherein that the at least one air intake opening is enlarged along the sides of the air intake plate.

31. A tanning module according to claim 30, wherein that the air intake opening is trapezoidal, the long side of the trapeze pointing to the reflector.

32. A tanning module according to claim 31, wherein that the long side of the trapeze and that of its opposite side are curved.

33. A tanning module according to claim 1, wherein that the at least one radiation filter is of rectangular configuration.

34. A tanning module according to claim 33, wherein that the at least one radiation filter has a length of from 215 mm to 240 mm and a width of from 215 mm to 240 mm.

35. A tanning module according to claim 34, wherein that the at least one radiation filter has a length of 230 mm and a width of 225 mm.

36. A tanning module according to claim 1, wherein that the at least one radiation filter is an interference filter.

37. A tanning module according to claim 36, wherein that a first radiation filter is present, and plane-parallel thereto a second radiation filter, the second radiation filter being disposed between the radiation issuance surface of the reflector and the first radiation filter, and the first radiation filter is the interference filter.

38. A tanning module according to claim 37, wherein that the second radiation filter is an ultraviolet filter or an infrared filter.

39. A tanning module according to claim 1, wherein that to safeguard against breakage of the at least one radiation filter at least one pushbutton switch is disposed on the housing and rests upon the at least one radiation filter.

40. A tanning module according to claim 39, wherein that the pushbutton switch is guided through the reflector perpendicular to the radiation issuance surface of the reflector.

41. A tanning module according to claim 39, wherein that the pushbutton switch is guided perpendicular to the radiation issuance surface of the reflector through an air intake plate.

42. A tanning module according to claim 1, wherein that the housing is rectangular in the area of the radiation filter and on all four sides it terminates in a lip, the four lips being aligned parallel to the radiation filter.

43. A tanning module according to claim 42, wherein that two oppositely lying lips of the four lips point toward the radiation filter.

44. A tanning module according to claim 43, wherein that the other two opposite lips of the four lips point away from the radiation filter.

\* \* \* \* \*